US009408726B2

(12) United States Patent
Rowe, Jr. et al.

(10) Patent No.: US 9,408,726 B2
(45) Date of Patent: Aug. 9, 2016

(54) SYSTEM AND METHOD FOR SEALING PROSTHETIC SOCKET

(71) Applicant: The Ohio Willow Wood Company, Mount Sterling, OH (US)

(72) Inventors: Larry Gail Rowe, Jr., Williamsport, OH (US); Lonnie LaVern Nolt, Washington Court House, OH (US); Jeffrey L. Doddroe, Washington Court House, OH (US); Jeffrey A. Denune, Galloway, OH (US)

(73) Assignee: THE OHIO WILLOW WOOD COMPANY, Mt. Sterling, OH (US)

( * ) Notice: Subject to any disclaimer, the term of this patent is extended or adjusted under 35 U.S.C. 154(b) by 13 days.

(21) Appl. No.: 14/341,430

(22) Filed: Jul. 25, 2014

(65) Prior Publication Data

US 2016/0022441 A1    Jan. 28, 2016

(51) Int. Cl.
*A61F 2/80* (2006.01)

(52) U.S. Cl.
CPC .............. *A61F 2/80* (2013.01); *A61F 2002/805* (2013.01)

(58) Field of Classification Search
CPC   A61F 2/80; A61F 2002/802; A61F 2002/805
See application file for complete search history.

(56) References Cited

U.S. PATENT DOCUMENTS

| | | | |
|---|---|---|---|
| 2,696,011 A | 12/1954 | Galdik | |
| 4,634,446 A * | 1/1987 | Kristinsson | A61F 2/80 623/33 |
| 4,908,037 A | 3/1990 | Ross | |
| 5,314,497 A | 5/1994 | Fay et al. | |
| 5,376,131 A | 12/1994 | Lenze et al. | |
| 5,735,906 A | 4/1998 | Caspers | |
| 5,904,722 A | 5/1999 | Caspers | |
| 6,361,568 B1 | 3/2002 | Hoerner | |
| 7,448,407 B2 | 11/2008 | Alley et al. | |
| 7,631,657 B2 | 12/2009 | Alley et al. | |
| 7,632,315 B2 | 12/2009 | Egilsson | |
| 7,850,739 B2 | 12/2010 | Perkins et al. | |
| 8,343,233 B2 | 1/2013 | Perkins et al. | |
| 8,394,150 B2 | 3/2013 | Laghi | |
| 8,758,449 B2 | 6/2014 | Caspers | |
| 2008/0221705 A1 * | 9/2008 | Scussel | A61F 2/80 623/32 |
| 2010/0312360 A1 | 12/2010 | Caspers | |
| 2014/0058529 A1 | 2/2014 | Schober et al. | |
| 2014/0067084 A1 | 3/2014 | Soss et al. | |
| 2014/0067085 A1 * | 3/2014 | Doddroe | A61F 2/78 623/36 |
| 2014/0277585 A1 | 9/2014 | Kelley et al. | |
| 2014/0379097 A1 | 12/2014 | Hurley et al. | |
| 2015/0051711 A1 * | 2/2015 | Egilsson | A61F 2/80 623/33 |

* cited by examiner

*Primary Examiner* — Bruce E Snow
(74) *Attorney, Agent, or Firm* — Benesch, Friedlander, Coplan & Aronoff LLP

(57) ABSTRACT

Various embodiments of a system and method for sealing a prosthetic socket are disclosed. One example socket sealing system may comprise: a prosthetic socket having a proximal end, an expanded section, and an internal peripheral shoulder; a brim seal having an inner proximal end, an outer proximal end, and a distal end; a removable brim having a distal end; a liner; and a wicking sock; wherein prosthetic socket may be oriented radially outwardly of the outer proximal end of the brim seal, the outer proximal end of the brim seal may be oriented radially outwardly of the removable brim, the removable brim may be oriented radially outwardly of the inner proximal end of the brim seal, the inner proximal end of the brim seal may be oriented radially outwardly of the wicking sock, and the wicking sock may be oriented radially outwardly of the liner; and wherein the brim seal may be reflected about the distal end of the removable brim.

8 Claims, 13 Drawing Sheets

SYSTEM AND METHOD FOR SEALING PROSTHETIC SOCKET

BACKGROUND

In prosthetics, an amputee normally dons a prosthetic device by inserting his/her residual limb into a socket portion of the prosthesis. Often, an amputee first places a prosthetic liner over the residual limb, after which the residual limb is inserted into the prosthetic socket, the prosthetic liner acting at least as a cushioning interface between the limb and socket. One example liner is the Alpha® Liner series of prosthetic liners from the Ohio Willow Wood Company in Mt. Sterling, Ohio.

Regardless of the selected limb preparation, the prosthesis must be securely retained on the residual limb in order to permit proper prosthesis function and amputee comfort. Often, in the case of vacuum suspension, a liner-covered residual limb is inserted into a prosthetic socket. A suspension sleeve may also be placed over the brim portion of the socket so as to overlie both the socket exterior and a portion of the residual limb (or liner). In this manner, air may be prevented from entering or exiting the socket from the proximal end of the socket, thereby facilitating the creation and maintenance of a vacuum within the socket. A vacuum device can be used to evacuate the socket interior to some desired vacuum level, so that the force of the vacuum holds the prosthetic socket (and prosthesis) on the residual limb.

The ability to generate and maintain a vacuum may be critical in the case of prosthetic vacuum suspension. If an adequate vacuum level cannot be produced within the socket, the associated prosthesis may not be properly secured to the residual limb. If vacuum is lost during use of the prosthesis, the prosthesis may become loose, leading to possible discomfort or malfunction. Adequately sealing a prosthetic socket can be difficult in the case of a below-knee, i.e., trans-tibial, (TT) amputee. However, these difficulties are often compounded in the case of an above-knee, i.e., trans-femoral (TF) amputee.

More specifically, no effective vacuum solutions have been developed for TF amputees. As compared to TT sockets, TF sockets do not have sufficient room above the brim of the socket for sealing to the liner. As a result, the liner must be reflected over the brim of the socket and then sealed to the socket with a sleeve. This technique may not be durable because amputees commonly bump the brim of the socket against hard objects, which may damage the liner and/or the sleeve, which may result in leakage and loss of vacuum. Furthermore, the presence of a bulky sealing sleeve near or in the groin area may be quite uncomfortable to an amputee.

Internal sealing systems have been developed for TF prostheses, but all known systems have unacceptable drawbacks. These drawbacks include, without limitation: that the seal may require an intimate fit to the residual limb and may not be effective if the limb shrinks or moves in such a way as to break the seal; that the seal may reside too low within the socket, and resulting vacuum suspension may thereby concentrate over too small of an area of the residual limb; and that the sealing element may be too restrictive and may need to be fit very carefully to avoid a constricting "tourniquet effect" on the residual limb.

What is needed is an improved vacuum suspension sealing system, especially an improved vacuum suspension sealing system for a TF prosthesis.

SUMMARY

In one embodiment, a socket sealing system is provided, the socket sealing system possibly comprising: a prosthetic socket having a proximal end, an expanded section, and an internal peripheral shoulder; a brim seal having an inner proximal end, an outer proximal end, and a distal end; a removable brim having a distal end; a liner; and a wicking sock; wherein prosthetic socket may be oriented radially outwardly of the outer proximal end of the brim seal, the outer proximal end of the brim seal may be oriented radially outwardly of the removable brim, the removable brim may be oriented radially outwardly of the inner proximal end of the brim seal, the inner proximal end of the brim seal may be oriented radially outwardly of the wicking sock, and the wicking sock may be oriented radially outwardly of the liner; and wherein the brim seal may be reflected about the distal end of the removable brim.

In one embodiment, a method for donning a socket sealing system, the method possibly comprising: providing a residual limb; donning a liner on the residual limb; donning a wicking sock on the residual limb radially outwardly of the liner; donning a brim seal on the residual limb proximal to the wicking sock; donning a removable brim on the residual limb radially outwardly of the brim seal; reflecting the brim seal about a distal end of the removable brim; and inserting the residual limb into a prosthetic socket.

In one embodiment, a distal bypass valve is provided, the distal bypass valve possibly comprising: a release base having an interior channel including a female thread; a release valve body having an interior channel, at least one relief channel, and an external surface having a male thread; a bypass valve having an interior channel; and an O-ring; wherein the male thread of the release valve body may engage the female thread of the release base; and wherein the at least one relief channel may provide a channel for air to travel between the release valve body and the release base.

BRIEF DESCRIPTION OF THE DRAWINGS

The accompanying figures, which are incorporated in and constitute a part of the specification, illustrate various example systems and methods and are used merely to illustrate various example embodiments. In the figures, like elements bear like reference numerals.

DETAILED DESCRIPTION

Figure 1:
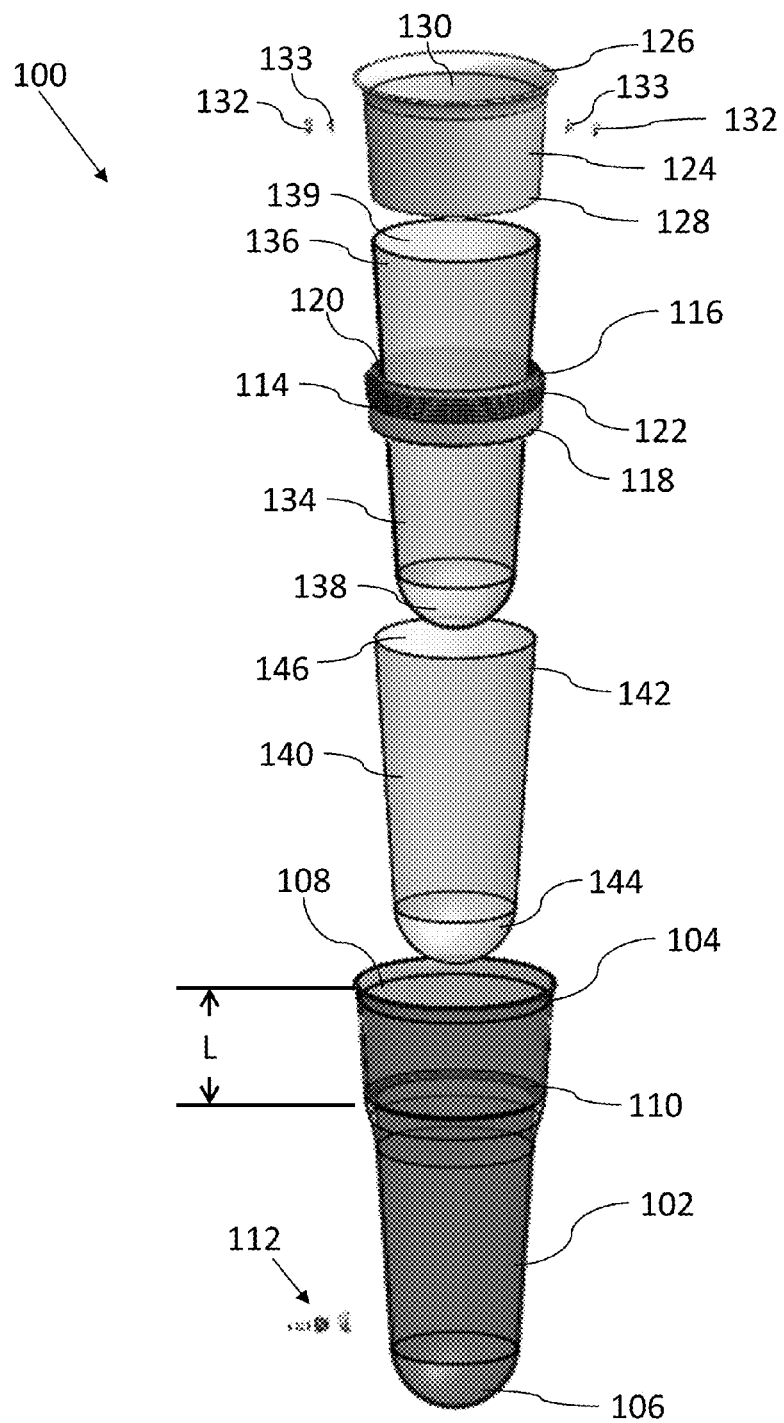
FIG. 1 is an exploded perspective view of an example embodiment of a socket sealing system.

FIG. 1 illustrates an exploded perspective view of an example embodiment of a socket sealing system 100. System 100 may include a socket 102 having a proximal open end 104 and a distal closed end 106. Socket 102 may include an expanded interior section 108, having a length L, which may result in a peripheral shoulder 110 within socket 102. Socket 102 may include a distal bypass valve 112. System 100 may include a brim seal 114 having a proximal end 116, a distal end 118, internal sealing pattern 120, and external sealing fins 122. System 100 may include a removable brim 124 having a proximal end 126 and a distal end 128. Removable brim 124 may include an interior surface 130, at least one locking button 132, and at least one nut 133. System 100 may include a liner 134 having a proximal open end 136, a distal closed end 138, and an interior surface 139. System 100 may include a wicking sock 140 having a proximal open end 142, a distal closed end 144, and an interior surface 146.

System 100 may be configured for use as a TF prosthesis. System 100 may be configured for use as a TT prosthesis. System 100 may be configured for use as an upper extremity prosthesis. System 100 may be configured for use with vacuum suspension.

Socket 102 may be any of a variety of prosthetic sockets. Socket 102 may be configured to accept a residual limb (not shown). Socket 102 may be configured to accept at least a portion of an amputee's leg. Socket 102 may be configured to accept at least a portion of an amputee's arm. Socket 102 may be substantially cylindrical in shape. Socket 102 may be substantially non-cylindrical in shape. Socket 102 may include any of a variety of shapes. Socket 102 may be constructed of a material that is substantially impervious to air. Socket 102 may be constructed of a material that is substantially rigid.

Socket 102 may include proximal open end 104. Proximal open end 104 may be of a diameter appropriate to accommodate an amputee's residual limb. Socket 102 may include a distal closed end 106. In one embodiment, distal end 106 is at least partially open.

Socket 102 may include expanded interior section 108. Expanded section 108 may include a greater dimension than the interior periphery of socket 102 at a more distal location. Expanded section 108 may be oriented substantially proximally in socket 102. Expanded section may create peripheral shoulder 110 within socket 102. Peripheral shoulder 110 may result from a difference in dimension between expanded section 108 and the interior periphery of socket 102 adjacent to, and distal to, expanded section 108.

Expanded section 108 may have a length L. Length L may be measured substantially longitudinally along socket 102. Length L may be measured from peripheral shoulder 110 to proximal end 104.

Expanded section 108 may be configured to accommodate at least one of removable brim 124 and brim seal 114 reflected about distal end 128 of removable brim 124.

Socket 102 may include distal bypass valve 112. Distal bypass valve 112 may be oriented at or near distal end 106 of socket 102. Distal bypass valve 112 may be configured to selectively allow ambient air into the interior of socket 102 when socket 102 is to be doffed from the amputee's residual limb.

Brim seal 114 may be substantially cylindrical in shape. Brim seal 114 may be comprised of any of a variety of materials, including for example an elastomer such as a silicone, a urethane, a latex, and the like. Brim seal 114 may comprise a reinforcement weave. Brim seal 114 may be coated with a substance, such as parylene, to create a thin, slick surface to aid in donning of system 100. Brim seal 114 may be configured to provide a seal between socket 102 and liner 134. Brim seal 114 may be stretched over a residual limb to seal against the exposed elastomer of liner 134.

Brim seal 114 may include internal seal pattern 120 to increase a contact pressure at the interface between brim seal 114 and liner 134. Internal seal pattern 120 may include a wave pattern. The point contact of each peak of seal pattern 120 may reduce the amount of surface area exposed to liner 134, and thus increase the amount of contact pressure between brim seal 114 and liner 134. This increased contact pressure may act to improve the sealing between brim seal 114 and liner 134, thus reducing leakage between brim seal 114 and liner 134. Seal pattern 120 of brim seal 114 may alternatively, or additionally, act as multiple sealing bands, which may improve the seal performance. In one embodiment, seal pattern 120 is oriented on an interior of brim seal 114. Seal pattern 120 may be arranged circumferentially about a portion of the interior of brim seal 114.

Brim seal 114 may include at least one external sealing fin 122. Sealing fin 122 may be configured to interface with the interior periphery of socket 102. Removable brim 124 may assist in holding sealing fin 122 into contact with socket 102. In one embodiment, sealing fin 122 is oriented on an interior of brim seal 114. Sealing fin 122 may be arranged circumferentially about a portion of the interior of brim seal 114. Sealing fin 122 may be oriented near one end of brim seal 114, while seal pattern 120 may be oriented near an opposite end of brim seal 114, such that when brim seal 114 is reflected about distal end 128 of removable brim 124, seal pattern 120 is oriented radially inwardly while sealing fin 122 is oriented radially outwardly.

Removable brim 124 may include proximal end 126, distal end 128, and an interior surface 130. Proximal end 126 and distal end 128 may be substantially open. Removable brim 124 may comprise a flexible material. Removable brim 124 may be configured to provide a comfortable interface between an amputee's anatomy and a rigid edge of socket 102.

Removable brim 124 may be selectively removable to allow access to brim seal 114, where brim seal 114 is at least partially oriented radially inward of removable brim 124. Removable brim 124 may be selectively removable to permit placement and orienting of brim seal 114, to permit internal positioning of brim seal 114. Internal positioning of brim seal 114 may help prevent contact of brim seal 114 with external forces, which may result in pinching and punctures. Internal positioning of brim seal 114 may prevent brim seal 114 from being punctured as a result of contact with car doors, door jambs, chairs, furniture, and the like.

Removable brim 124 may hold brim seal 114 in place upon donning of system 100. Removable brim 124 may create an interference fit between sealing fin 122 and the interior of socket 102. The removable nature of removable brim 124 may permit customization of system 100 on an amputee-by-amputee basis, including customization to account for limb circumference, and customization to permit placement of brim seal 114 in optimal orientation for a given amputee's limb.

Removable brim 124 may include at least one locking button 132 oriented on an exterior surface of removable brim 124. At least one locking button 132 may be held in place by at least one fastener, such as nut 133. Nut 133 may be replaced with any of a variety of fasteners capable of retaining locking button 132 on removable brim 124, including a screw, an adhesive, a boss, a rivet, a pin, an interference fit, and the like. Removable brim 124 may include two locking buttons 132. Removable brim 124 may include two or more locking buttons 132. Removable brim 124 may include three or more locking buttons 132.

At least one locking button 132 may be configured to at least partially engage a slot (not shown) in socket 102. The slot may include a hole through the wall of socket 102, an indention on the interior wall of socket 102, a groove on the interior wall of socket 102, and the like. The engagement between at least one locking button 132 and the slot may selectively secure removable brim 124 to socket 102. The engagement between at least one locking button 132 and the slot may allow a small degree of misalignment between removable brim 124 and socket 102 so as to aid in assembly of system 100 by an amputee. The small degree of misalignment allowable may be between about four and ten degrees.

Engagement of at least one locking button 132 with a slot in socket 102 may result in an audible "click" to indicate proper assembly to the amputee. Where at least one locking button 132 engages one or more hole in socket 102, an amputee can visually and/or tactilely confirm engagement between at least one locking button 132 and the one or more hole in socket 102, and thus the amputee can confirm proper assembly of system 100. Engagement of at least one locking button 132 with the one or more slot may ensure that appropriate clearance inside socket 102 exists. Engagement of at least one locking button 132 with the one or more slot may ensure that a minimal void exists between removable brim 124 and peripheral shoulder 110 within socket 102 into which an amputee's limb may be drawn.

At least one locking button 132 may be easily disengaged by an amputee during doffing of system 100. For example, an amputee may press at least one locking button 132 radially inward toward liner 140 and the residual limb so as to permit clearance of at least one locking button 132 to disengage the slot in socket 102.

Liner 134 may include proximal open end 136, distal closed end 138, and interior surface 139. In one embodiment, distal end 138 is open. Liner 134 may be the first component of system 100 donned over the amputee's residual limb. As a result, liner 134 may directly contact the amputee's residual limb.

Liner 134 may comprise any of a variety of materials, including for example a soft elastomer. Liner 134 may not include any fabric portion, but rather, may include simply a homogenous makeup of elastomer. The lack of any fabric may provide an exterior surface of liner 134 capable of sealing in a vacuum environment. Alternatively, at least a portion of liner 134 may include a fabric outer covering.

Liner 134 may comprise an elastomer that is naturally very tacky. Such a tacky elastomer may make it difficult for liner 134 to slide on itself when donning. Accordingly, liner 134 may include a coating of parylene on at least its outer surface to create a very thin, slick coating. Interior surface 139 may be left tacky to improve adherence between liner 134 and the amputee's residual limb, so as to prevent sliding or movement, which may cause skin irritation.

Wicking sock 140 may include proximal open end 142, distal closed end 144, and interior surface 146. In one embodiment, distal end 144 is open. Wicking sock 140 may be donned directly over liner 134. Wicking sock 140 may be configured to provide an air wick, thereby allowing air to escape through wicking sock 140, and a vacuum to be evenly applied throughout the interior of socket 102. In one embodiment, wicking sock 140 is integral to liner 134. In another embodiment, wicking sock 140 is separate from liner 134. Where liner 134 is used without a fabric covering, wicking sock 140 can be applied over liner 134 to ensure that air is not trapped in pockets between liner 134 and socket 102.

A practitioner or amputee may trim the length of wicking sock 140 to customize where the exposed sealing surface of liner 134 begins. The ability to customize the length of wicking sock 140 may maximize the amount of limb surface area under vacuum for a given amputee.

Wicking sock 140 may comprise any of a variety of fabrics. Wicking sock 140 may include a fabric designed to maximize airflow. Wicking sock 140 may include a fabric designed to stabilize the shape of a residual limb. Wicking sock 140 may include a fabric designed to both maximize airflow and stabilize the shape of a residual limb. Wicking sock 140 may be designed so as to easily stretch circumferentially to match the size of an amputee's residual limb. Wicking sock 140 may be designed so that it has limited longitudinal stretch to limit limb elongation. An amputee's residual limb can be stretched during donning of system 100 and/or during ambulation, which may create discomfort over time. Accordingly, it may be desirable to avoid elongation of the residual limb.

Wicking sock 140 may comprise a thin elastomeric coating on interior surface 146. The thin elastomeric coating may stick to liner 134 for a more intimate fit. Wicking sock 140 may be made in varying thickness and/or with varying thickness of elastomeric coating. Varying the thickness of wicking sock 140 and/or the elastomeric coating may allow one to provide additional cushioning within system 100. Varying the thickness of wicking sock 140 and/or the elastomeric coating may allow one to compensate for socket fit variations where necessary. Pads can be located between wicking sock 140 and liner 134. The pads can be used to provide additional cushioning and/or compensate for socket fit variations where necessary. Orienting the pads between wicking sock 140 and liner 134 may substantially prevent migration of the pads.

Figure 2:
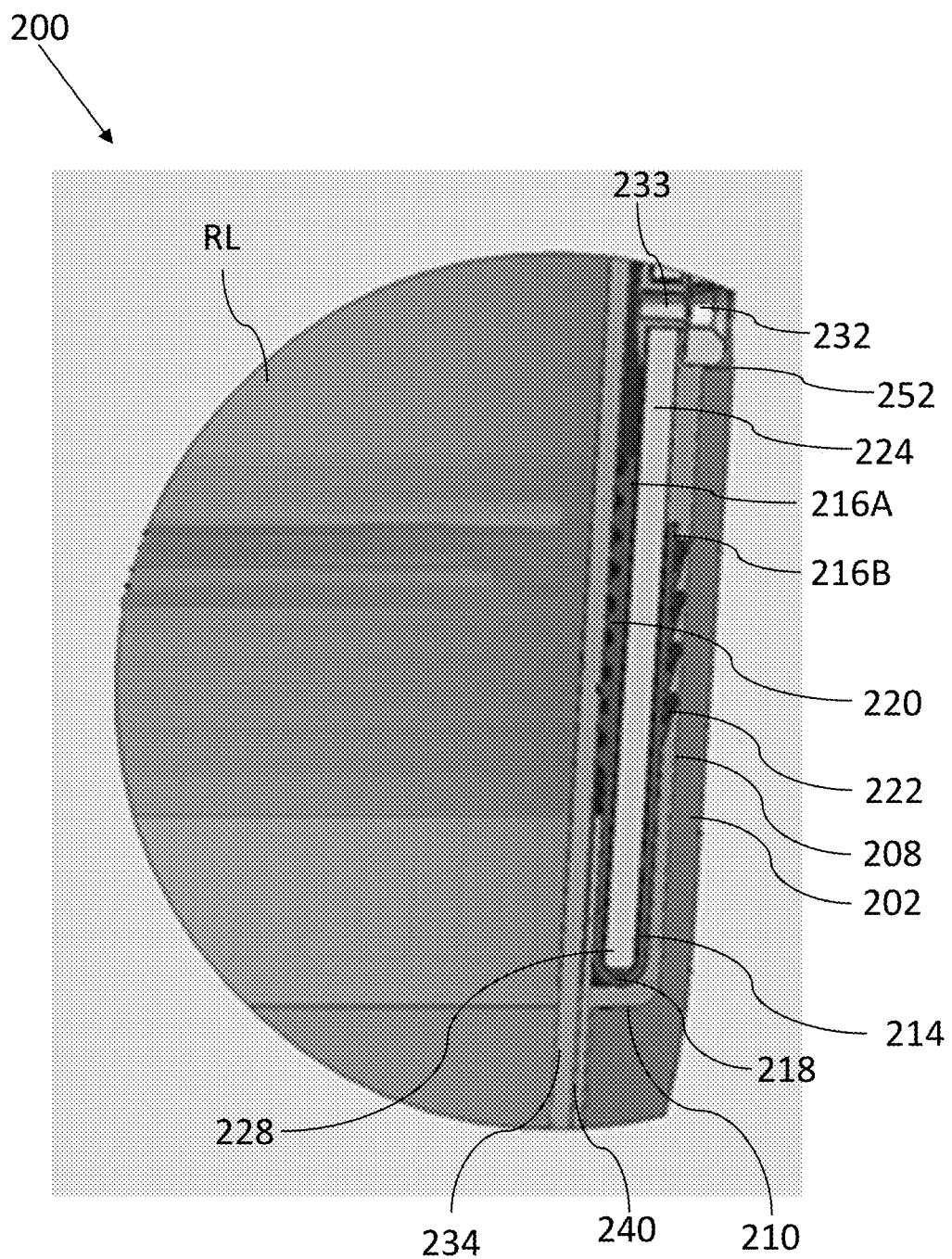
FIG. 2 is a partial sectional view of an example embodiment of a socket sealing system.
Figure 2A:
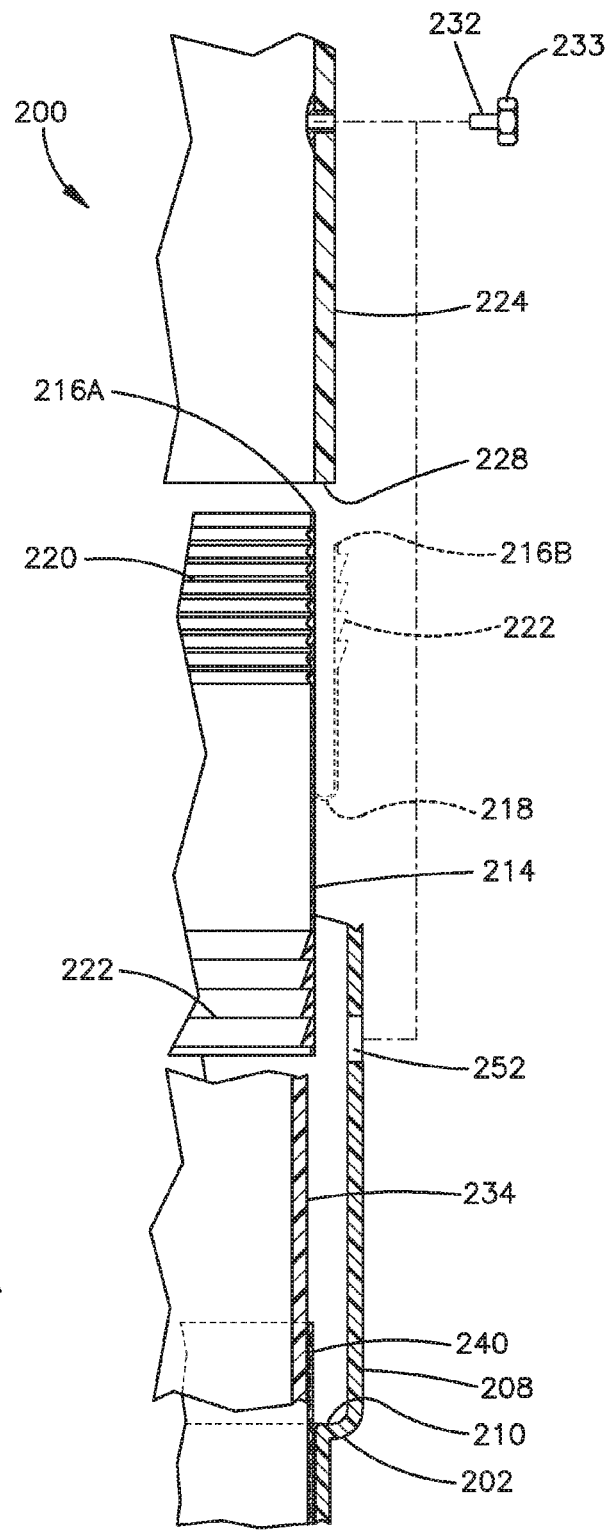
FIG. 2A is an exploded view of the components shown in FIG. 2.

FIG. 2 is a partial sectional view of an example embodiment of a socket sealing system 200. While FIG. 2 is a sectional view of a portion of socket sealing system 200, it is understood that the sealing mechanisms described herein extend about the circumference of a socket 202 to completely seal socket. It is further understood that system 200 may be representative of the various components of system 100 assembled and donned on a residual limb RL. This is indicated by FIG. 2A, which shows the components of FIG. 2 in an exploded view similar to FIG. 1.

System 200 may include socket 202. Socket 202 may include an expanded section 208. Socket 202 may include a peripheral shoulder 210. System 200 may include a brim seal 214 having an inner proximal end 216A, an outer proximal end 216B, and a distal end 218. Brim seal 214 may include an internal sealing pattern 220 and at least one external sealing fin 222. System 200 may include a removable brim 224. Removable brim 224 may include a distal end 228. Removable brim 224 may include at least one locking button 232 attached to removable brim 224 by a nut 233. System 200 may include a liner 234. System 200 may include a wicking sock 240. Socket 202 may include a hole 252 for engaging at least one locking button 232.

System 200 includes residual limb RL. Liner 234 is applied to residual limb RL, such that liner 234 directly contacts residual limb RL.

Wicking sock 240 may be applied over at least a portion of liner 234. Wicking sock 240 may be of a length such that wicking sock 240 extends from a distal end (not shown) of socket 202 to a point distal of internal sealing pattern 220. Preventing wicking sock 240 from extending to internal sealing pattern 220 ensures proper engagement between internal sealing pattern 220 and liner 234.

The ability to remove removable brim 224 may permit inner proximal end 216A of brim seal 214 to extend in a proximal direction rather than a distal direction. During use, system 200 will be applied to a vacuum such that the interior of socket 202 is evacuated to a preferred vacuum level. Ambient air, at ambient pressure, will naturally attempt to enter the interior of socket 202. As socket 202 is only substantially open on its proximal end (not shown), ambient air will be pushed to enter socket 202 from a point proximal to inner proximal end 216A of brim seal 214.

Proximally-extending inner proximal end 216A is more resistant to leakage than a distally-extending inner proximal end (not shown). A distally-extending inner proximal end (not shown) may be pushed away from liner 234 by ambient air, thus allowing air to leak into the interior of socket 202. Proximally-extending inner proximal end 216A, to the contrary, engages liner 234 more intimately upon application of ambient pressure from ambient air. Additionally, friction and shear stresses between proximally-extending inner proximal end 216A, including its internal sealing pattern 220, and liner 234 make proximally-extending inner proximal end 216A less likely to shift or slip relative to liner 234.

Additionally, outer proximal end 216B may be oriented to extend in a proximal direction rather than a distal direction. During donning, residual limb RL, including liner 234, wicking sock 240, brim seal 214, and removable brim 224 may be inserted into socket 202 from a proximal end (not shown) of socket 202 toward a distal end (not shown) of socket 202. As a result, outer proximal end 216B and at least one external sealing fin 222 are oriented in a proximal direction. For the same reasons described above with respect to inner proximal end 216A, a proximally-extending outer proximal end 216B is more resistant to leakage.

Brim seal 214 may be reflected about distal end 228 of removable brim 224. Brim seal 214 and distal end 228 of removable brim 224 may be configured to engage peripheral shoulder 210. Engagement of brim seal 214 and distal end 228 of removable brim 224 with peripheral shoulder 210 may prevent removable brim 224 from extending too far into socket 202. Upon reaching the proper orientation between removable brim 224 and socket 202, at least one locking button 232 may engage at least one hole 252, thus notifying an amputee donning system 200 that the assembly is complete and oriented correctly.

Residual limb RL may provide force against liner 234 in a radially outward direction. Removable brim 224 may provide force against brim seal 214 and internal sealing pattern 220 in a radially inward direction. As a result, residual limb RL and removable brim 224 may press liner 234, and brim seal 214 and sealing pattern 220, into more intimate engagement with one another so as to resist leakage.

Similarly, removable brim 224 may provide force against brim seal and at least one external sealing fin 222 in a radially outward direction, thereby causing more intimate engagement of external sealing fin 222 with socket 202 so as to resist leakage.

Figure 3A:
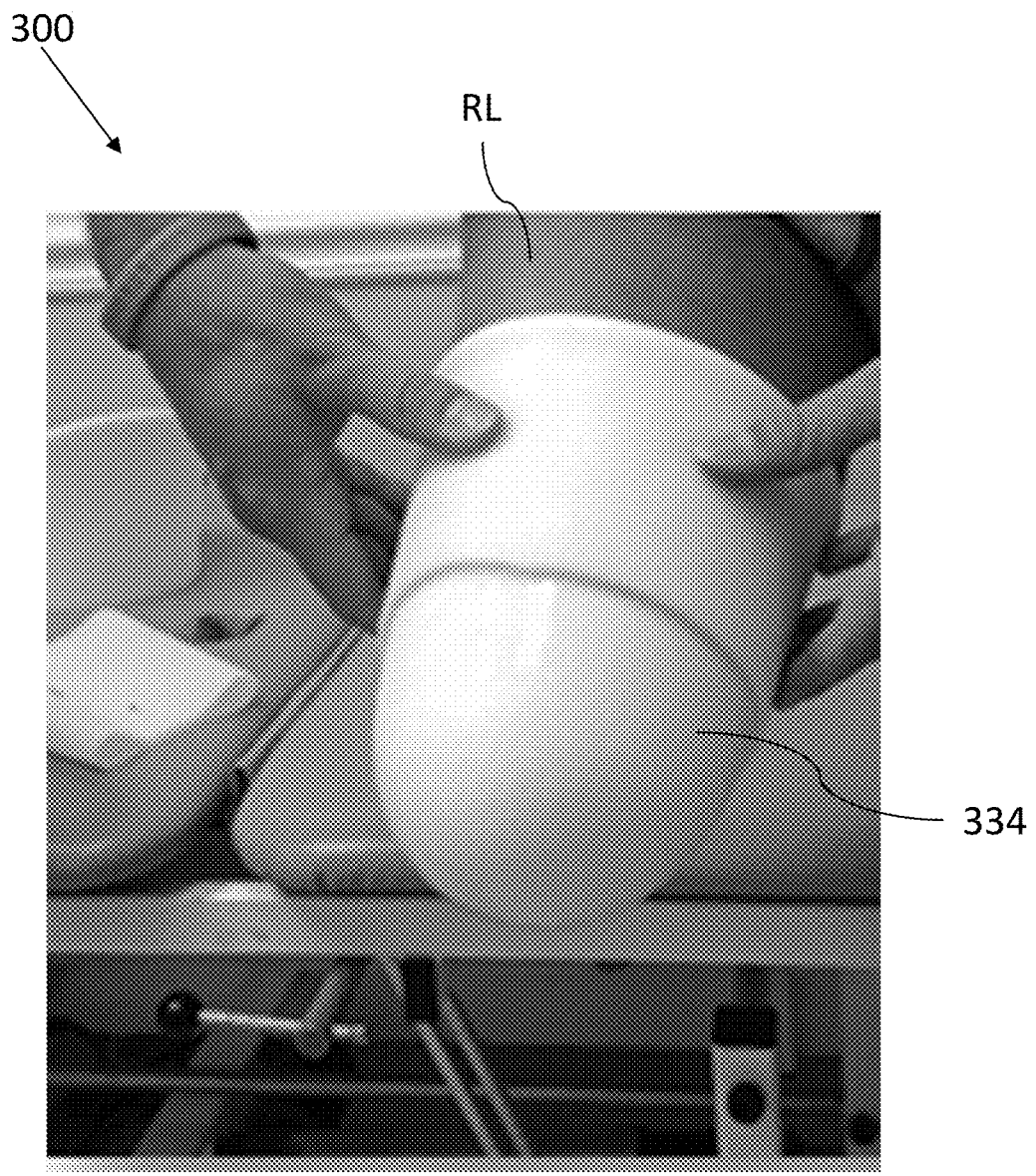
FIG. 3A is a perspective view of a liner 334 being donned on a residual limb RL.

FIG. 3A is a perspective view of a liner 334 being donned on a residual limb RL. Liner 334 may be turned inside-out and its distal end placed against the distal end of residual limb RL. An amputee may pull liner 334 proximally, allowing it to reflect over itself and roll onto residual limb RL. Liner 334 may be coated on its exterior surface with a parylene coating, or any other like lubricating coating, so as to permit sliding of its exterior surface along itself. Liner 334 may be rolled onto residual limb RL until the entirety of liner 334 is donned on residual limb RL in a non-reflected orientation. Liner 334 may include an exterior surface comprising an elastomer.

Figure 3B:
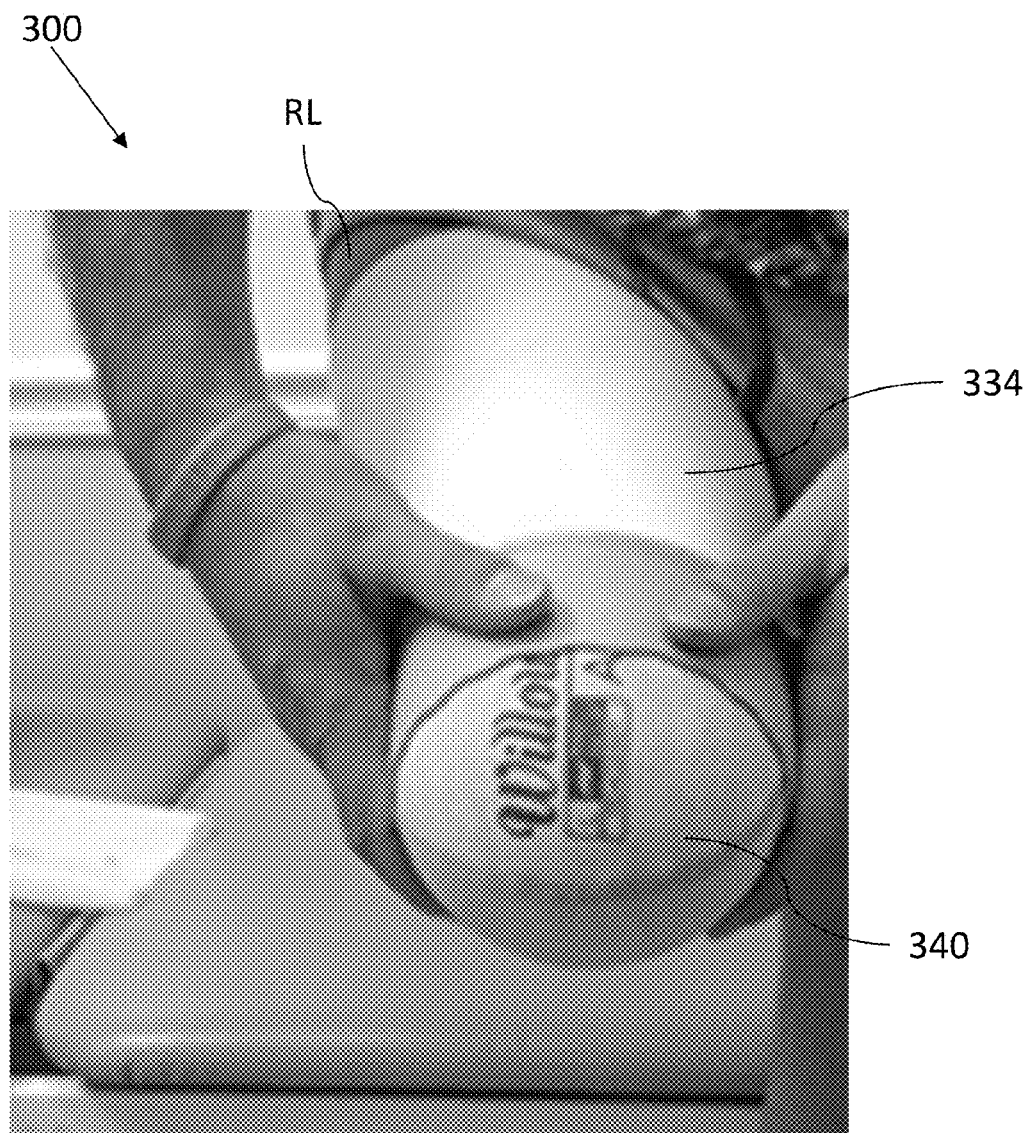
FIG. 3B is a perspective view of a wicking sock 340 being donned on residual limb RL.

FIG. 3B is a perspective view of a wicking sock 340 being donned on residual limb RL. Wicking sock 340, similar to liner 334, may be turned in-side out and rolled onto the exterior surface of liner 334 until the entirety of wicking sock 340 is donned on residual limb RL in a non-reflected orientation.

Figure 3C:
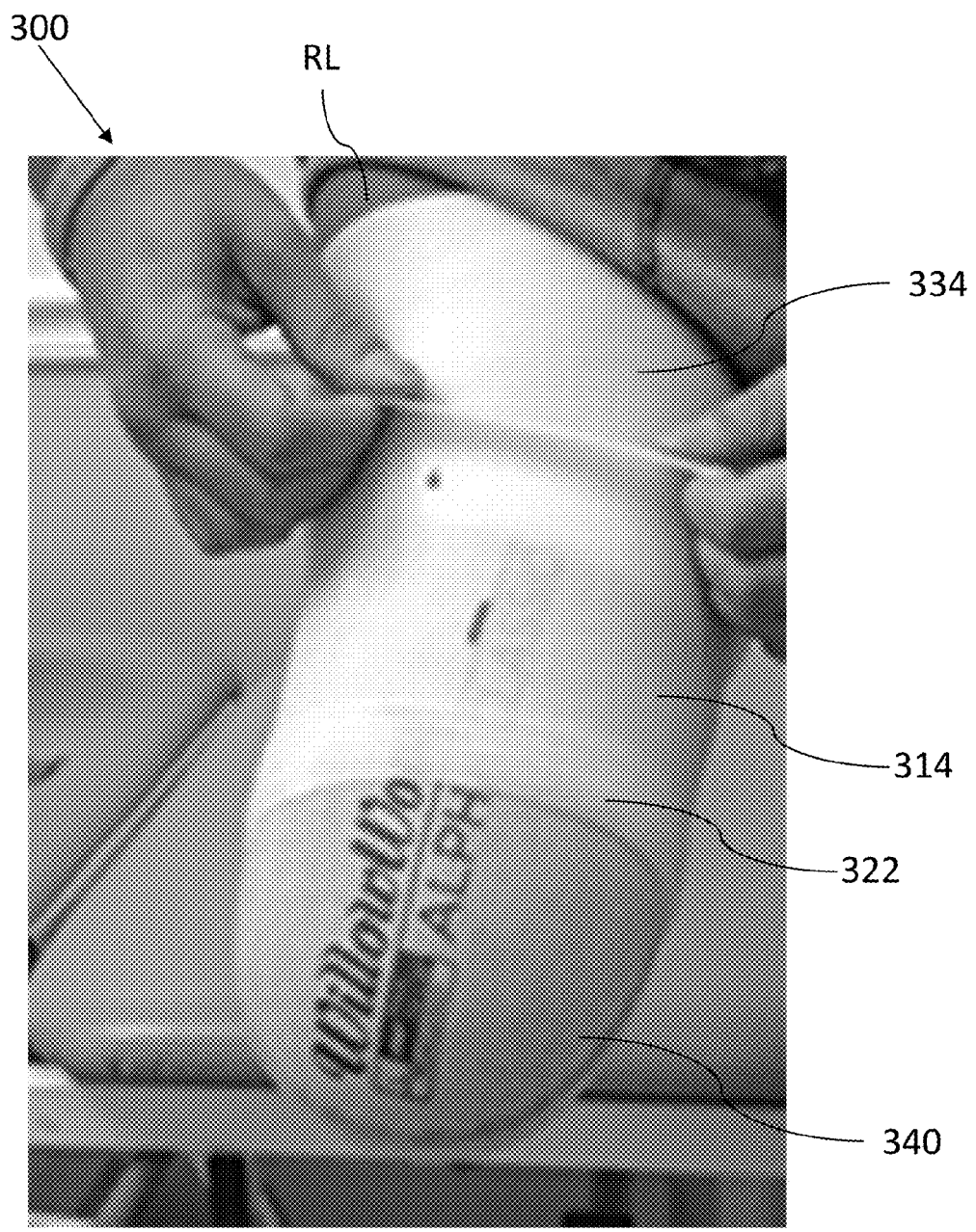
FIG. 3C is a perspective view of a brim seal 314 being donned on residual limb RL.

FIG. 3C is a perspective view of a brim seal 314 being donned on residual limb RL. Brim seal 314 may be turned inside-out and rolled onto wicking sock 340. Alternatively, brim seal 314 may be stretched over wicking sock 340 and advanced proximally. Brim seal 314 may be advanced proximally to a predetermined target location relative to the proximal end of wicking sock 340. Brim seal 314 may include at least one external sealing fin 322, which may be oriented radially inwardly until brim seal 314 is reflected about the distal end of a removable brim (not shown). A sealing pattern (not shown) may be oriented radially inwardly. Brim seal 314 may be oriented such that a sealing pattern (not shown) is oriented proximally. Brim seal 314 may be oriented such that at least one external sealing fin 322 is oriented distally.

Figure 3D:
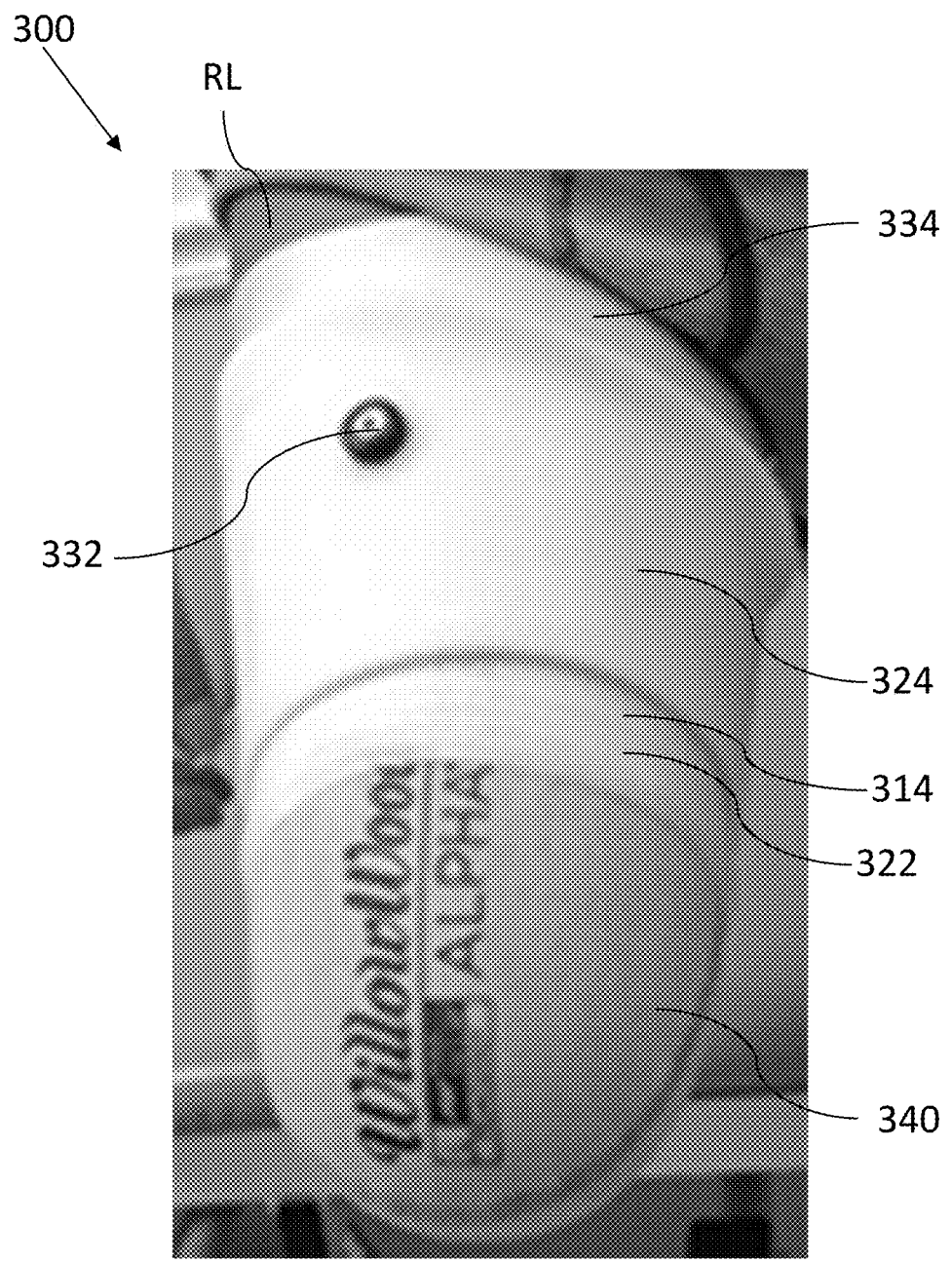
FIG. 3D is a perspective view of a removable brim 324 donned on residual limb RL.

FIG. 3D is a perspective view of a removable brim 324 donned on residual limb RL. Removable brim 324 may be donned from a distal end of residual limb RL and advanced proximally to a predetermined point. The distal end of removable brim 324 may be oriented proximally of at least one sealing fin 322 of brim seal 314. Removable brim 324 may include at least one locking button 332 configured to engage at least a portion of a socket (not shown).

Figure 3E:
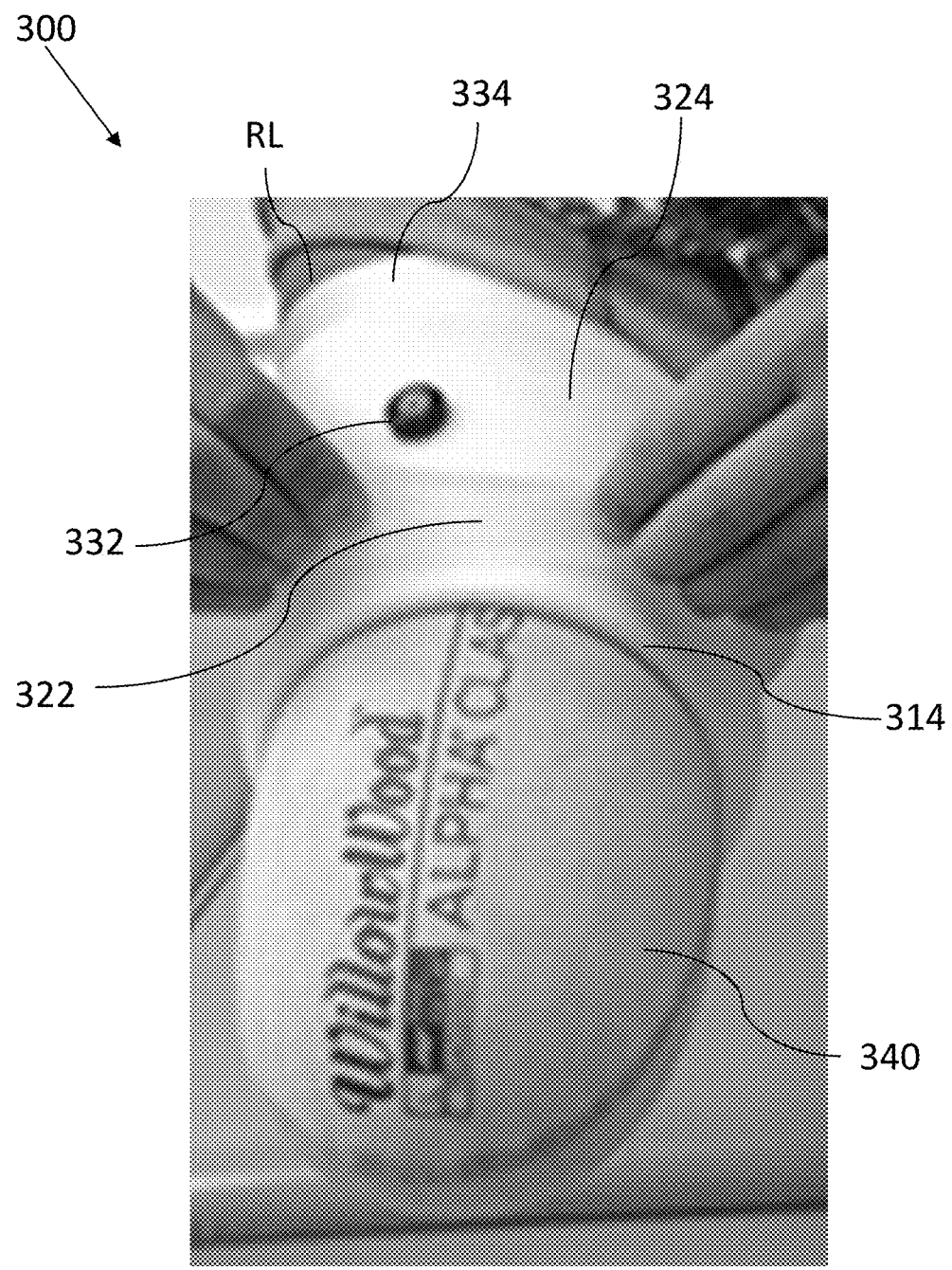
FIG. 3E is a perspective view of brim seal 314 being reflected over removable brim 324 on residual limb RL.

FIG. 3E is a perspective view of brim seal 314 being reflected over removable brim 324 on residual limb RL. Brim seal 314 may be reflected about the distal end of removable brim 324 such that at least one external sealing fin 322 is oriented radially outwardly.

Figure 3F:
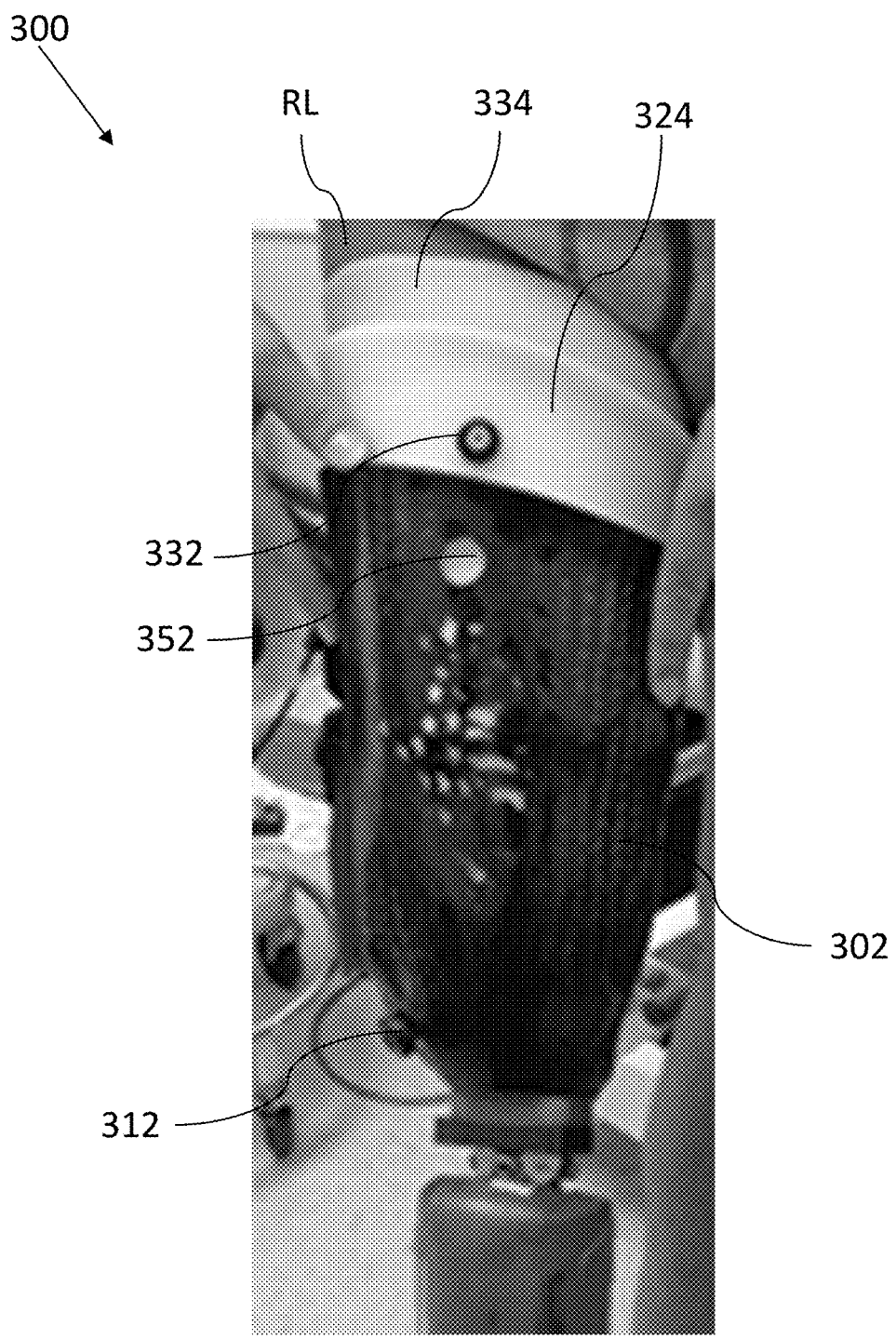
FIG. 3F is a perspective view of a socket 302 being donned on residual limb RL.

FIG. 3F is a perspective view of a socket 302 being donned on residual limb RL. Residual limb RL, including liner 334, and removable brim 324 may be inserted into socket 302. At least one locking button 332 may be rotationally aligned with a hole 352 in socket 302. Socket 302 may include at least one distal bypass valve 312. Distal bypass valve 312 may be opened during donning to allow air to escape the interior of socket 302 through distal bypass valve 312.

Figure 3G:
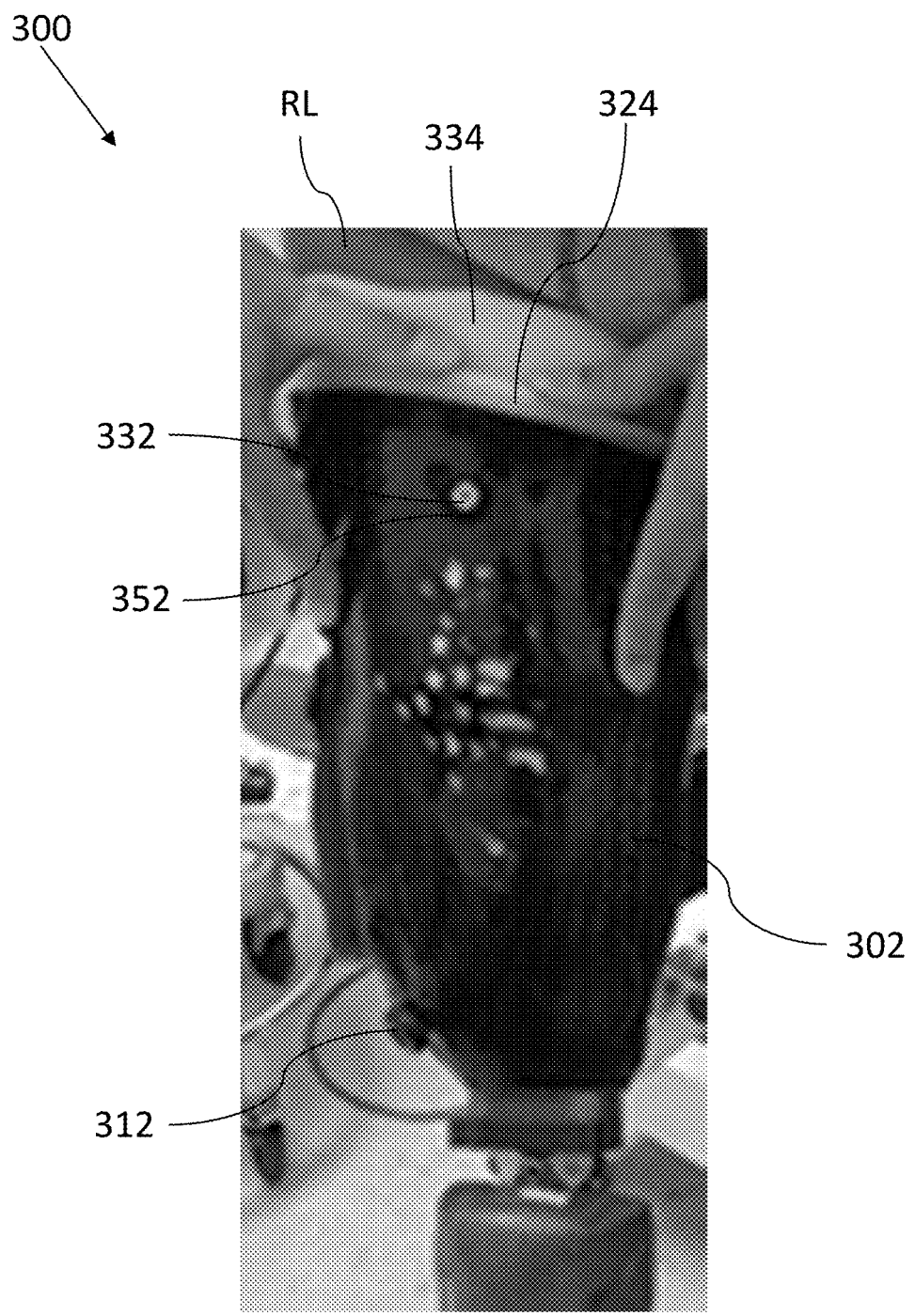
FIG. 3G is a perspective view of socket 302 donned on residual limb RL.

FIG. 3G is a perspective view of socket 302 donned on residual limb RL. Residual limb RL, including liner 334, and removable brim 324 may be inserted into socket 302 completely, such that at least one locking button 332 engages hole 352. With this, distal bypass valve 312 may be closed, and a vacuum applied to the interior of socket 302 so as to create a vacuum suspension of socket 302 on residual limb RL. In one embodiment, distal bypass valve 312 may be selectively opened to allow air to enter the interior of socket 302, thus destroying the vacuum therein and permitting the doffing of socket 302 from residual limb RL.

Socket sealing systems 100, 200, 300 may allow for the use of non-cylindrically shaped sockets 102, 202, 302, which permit an optimized fit to residual limb RL and prevent rotation relative to residual limb RL. This is in contrast to prior art systems that may require a substantially cylindrical shape socket 102, 202, 302 in order for the seal to function properly, which may result in limited resistance to rotation of socket 102, 202, 302 about residual limb RL. Socket sealing systems 100, 200, 300 may permit the use of sockets with lower trim lines, which may enhance range of motion, comfort, and life of liner 134, 234, 334. Socket sealing system 100, 200, 300 may result in a more comfortable and durable liner/socket system that maintains fit and performance during a wide range of activities and physical changes. The internally sealed socket 102, 202, 302 and vacuum suspension may provide amputees with superior suspension, maintain residual limb RL volume and socket fit, reduce skin breakdown, increase proprioception, and/or increase range of motion.

Figure 4:
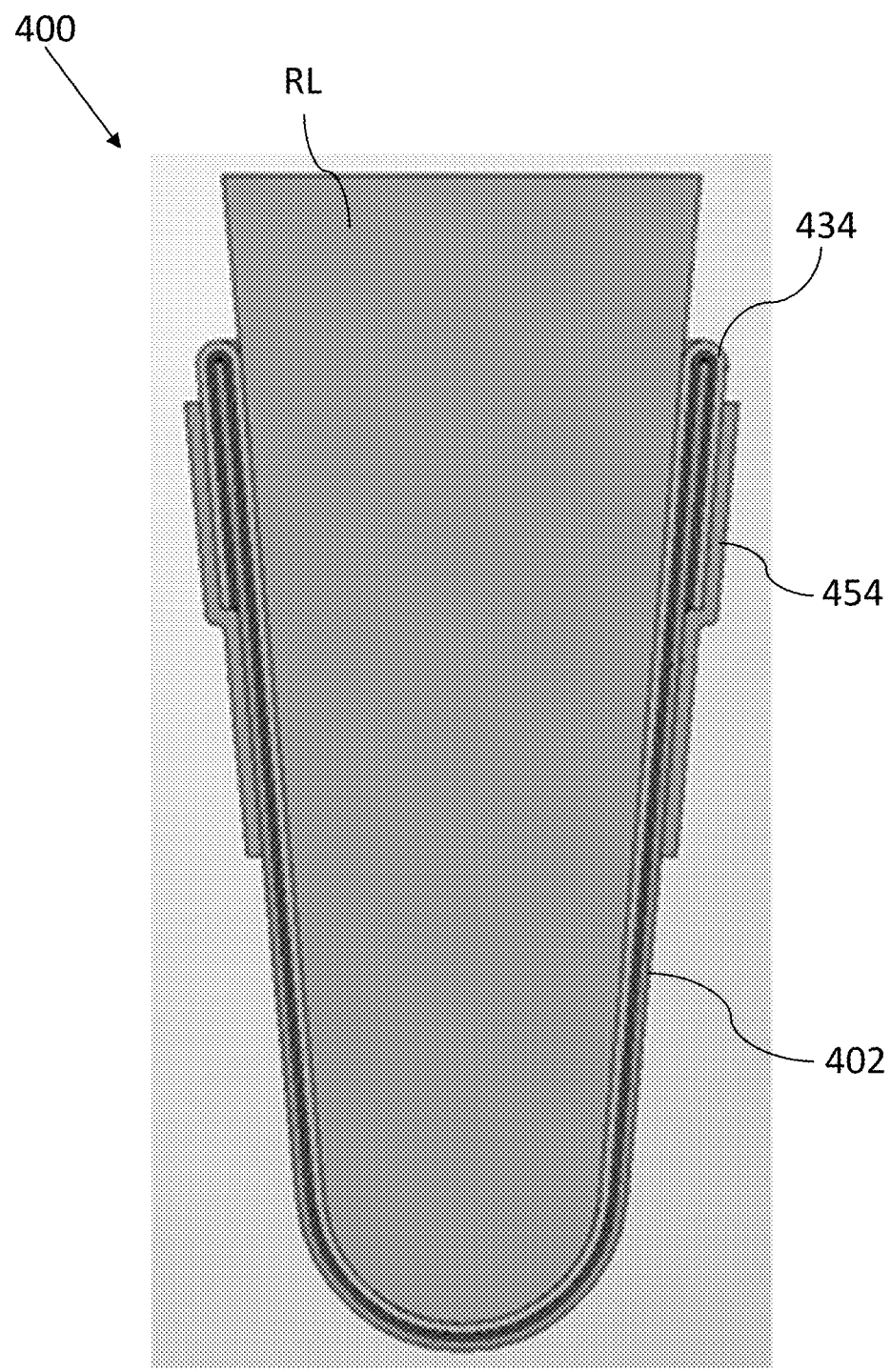
FIG. 4 is a sectional view of a prior art example embodiment of a socket sealing system.

FIG. 4 is a sectional view of a prior art example embodiment of a socket sealing system 400. System 400 includes a socket 402, an externally exposed liner 434, and an externally exposed sleeve 454.

System 400 may be representative of a prior art system for sealing a TF prosthetic suction or vacuum socket 402. Liner 434, which is longer than prosthetic socket 402, is rolled onto the residual limb RL. The proximal edge of liner 434 is flipped downwards over the proximal edge of socket 402. The inner elastomer of liner 434 is thereby exposed on the reflected portion of liner 434. Sleeve 454, which includes two open ends, is then placed over the exposed elastomer of the reflected liner 434 and the outside of socket 402 to create an air-tight seal.

However, in prior art system 400, sleeve 454 and the reflected portion of liner 434 are both exposed outside prosthetic socket 402. It is very easy for an amputee to bump into a hard object and puncture one or both of the reflected liner 434 and sleeve 454.

Accordingly, it may be beneficial to eliminate the exposed portions of liner 434 and sleeve 454 by placing the seal inside prosthetic socket 402. The rigid prosthetic socket 402 will then protect liner 434 and seal 454 from harm.

Figure 5A:
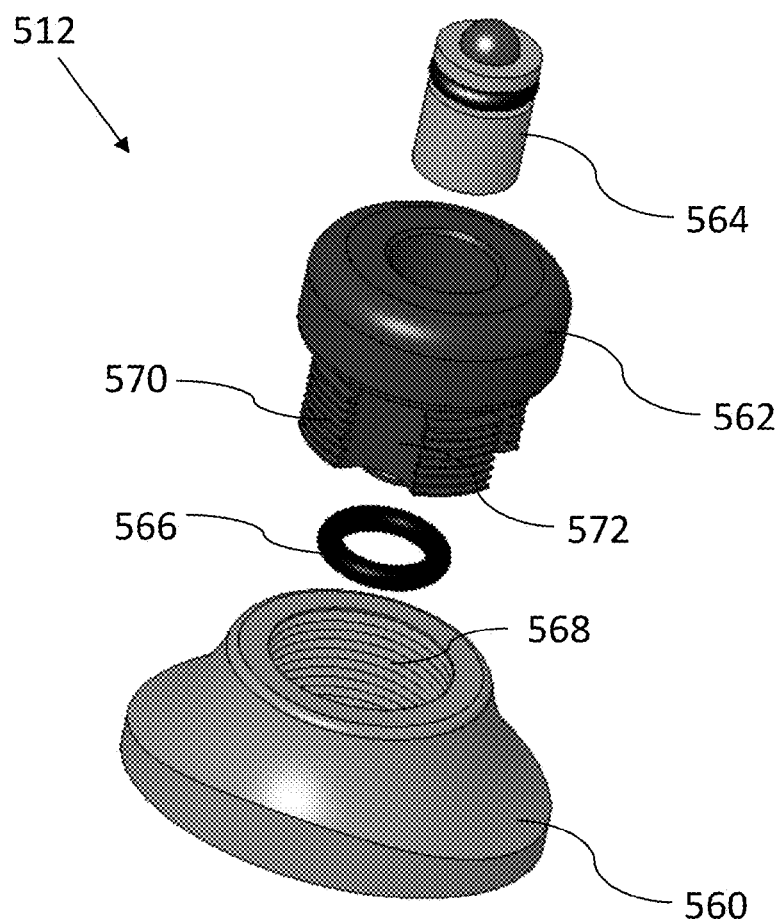
FIG. 5A is an exploded perspective view of an example embodiment of a distal bypass valve 512.
Figure 5B:
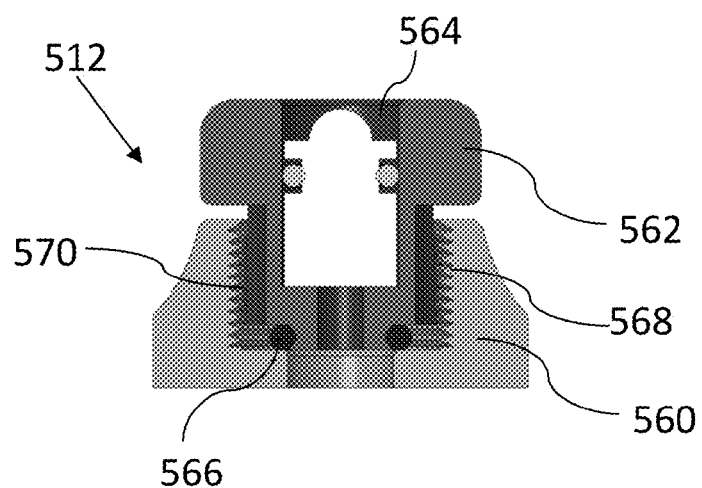
FIG. 5B is a sectional view of an example embodiment of distal bypass valve 512.

FIG. 5A is an exploded perspective view of an example embodiment of a distal bypass valve 512. FIG. 5B is a sectional view of an assembled example embodiment of distal bypass valve 512. Distal bypass valve 512 may include a release base 560. Distal bypass valve 512 may include a release valve body 562. Distal bypass valve 512 may include a bypass valve 564. Distal bypass valve 512 may include an O-ring 566.

Since the seal of system 100, 200, 300 described above are internal to the socket 102, 202, 302, a vacuum release mechanism (such as distal bypass valve 512) may be necessary for doffing socket 102, 202, 302. That is, distal bypass valve 512 may be incorporated into system 100, 200, 300 to permit the amputee to selectively allow air to enter socket 102, 202, 302 by opening distal bypass valve 512, thus destroying the vacuum therein and permitting the amputee to doff socket 102, 202, 302. In this embodiment, distal bypass valve 512 selectively allows air to enter socket 102, 202, 302.

Similarly, distal bypass valve 512 may be opened during donning of socket 102, 202, 302 to allow air within socket 102, 202, 302 to escape during insertion of the residual limb. In this embodiment, distal bypass valve 512 selectively allows air to exit socket 102, 202, 302.

Distal bypass valve 512 may be operatively connected to a socket, such as socket 102, 202, 302. Distal bypass valve 512 may be integrated into a socket, such as socket 102, 202, 302. Distal bypass valve 512 may be oriented in a substantially distal portion of a socket, such as socket 102, 202, 302. Distal bypass valve 512 may selectively permit air to pass through distal bypass valve 512. Distal bypass valve 512 may be a dual-directional valve, letting air pass from both a release base 560 end toward a bypass valve 564 end, and vice versa. Distal bypass valve 512 may automatically allow air to pass from a release base 560 end toward a bypass valve 564 end (thus allowing air to automatically exit a socket when distal bypass valve 512 is installed in a socket), while selectively allowing air to pass from a bypass valve 564 end toward a release base 560 end (thus allowing air to selectively enter a socket when distal bypass valve 512 is installed in a socket).

Release base 560 may be laminated into a socket, such as socket 102, 202, 302. Release base 560 may be connected to a socket, such as socket 102, 202, 302, via any attachment mechanism, including one or more threaded fastener, adhesives, rivets, a friction fit, and the like.

Release base 560 may comprise an interior channel having female threads 568. Release valve body 562 may include an external surface having male threads 570. Release base 560 may connected to release valve body 562 via threads 568 and 570. Alternatively, release base 560 may be connected to release valve body 562 through any attachment mechanism, including one or more threaded fastener, adhesives, rivets, a friction fit, and the like.

Release valve body 562 may include at least one relief channel 572. At least one relief channel 572 may be configured to selectively allow air to pass from outside a socket in which distal bypass valve 512 is installed, to the interior of the socket. O-ring 566 may be installed within a groove in the proximal edge of release valve body 562. O-ring 566 may be configured to seal off the proximal end of at least one relief channel 572, thus preventing air from passing through relief channel 572 when release valve body 562 is threaded into release base 560 far enough to cause O-ring 566 to contact release base 560.

Bypass valve 564 may be a one-way check valve, permitting air to pass from its proximal end, through bypass valve 564 itself, and out its distal end. Bypass valve 564 may be configured to prevent air from passing from its distal end toward its proximal end. Bypass valve 564 may be a ball check valve. Bypass valve 564 may be any of a variety of check valve types, including for example: a ball check valve, a swing check valve, a tilting disk check valve, a wafer-type check valve, a disk check valve, a piston check valve, a dual plate wafer check valve, and the like. Bypass valve 564 may be any valve capable of automatically allowing air to pass from one end to the other, while prevent air to pass the opposite direction. In one embodiment, bypass valve 564 is an ordinary valve manually operated by an amputee to selectively open and close.

As illustrated in FIG. 5B, the assembled distal bypass valve 512 may be connected at release base 560 to a socket (not shown). The socket may have a hole in fluid communication with the interior channel of release base 560. When donning the socket, the user may thread release valve body 562 into release base 560 far enough that O-ring 566 contacts release base 560 and seals at least one relief channel 572. When donning the socket, air from within the socket may pass through the hole in the socket, into the interior channel of release base 560, through an interior channel of release valve body 562, and through an interior channel of bypass valve 564 to the atmosphere. Bypass valve 564 may either automatically or manually open to allow air to pass in such a manner.

When doffing the socket, a user may unthread release valve body 562 from release base far enough to allow air to pass through at least one relief channel 572, past O-ring 566, through the interior channel of release base 560, through a hole in the socket, and thus into the socket. Distal bypass valve 512 may be designed such that release valve body 562 only need be unthreaded about 180 degrees to allow air to pass through distal bypass valve 512 from the atmosphere. Alternatively, distal bypass valve 512 may be designed such that release valve body 562 need be unthreaded more than 180 degrees or less than 180 degrees to allow air to pass through distal bypass valve 512 from the atmosphere.

Distal bypass valve 512 may additionally include a filter (not shown). A filter (not shown) may be oriented in release valve body 562. The filter may be configured to protect the valve from debris in air passing to the atmosphere during use of distal bypass valve 512. The filter may be configured to protect the valve from debris in air passing from the atmosphere during use of distal bypass valve 512.

In one embodiment, the filter (not shown) is attached to release valve body 562 and configured to filter air passing to the atmosphere, while moving out of the way and not filtering air passing from the atmosphere. In this embodiment, air entering a socket to which distal bypass valve 512 is attached is not impeded and/or slowed by the filter.

Figure 6:
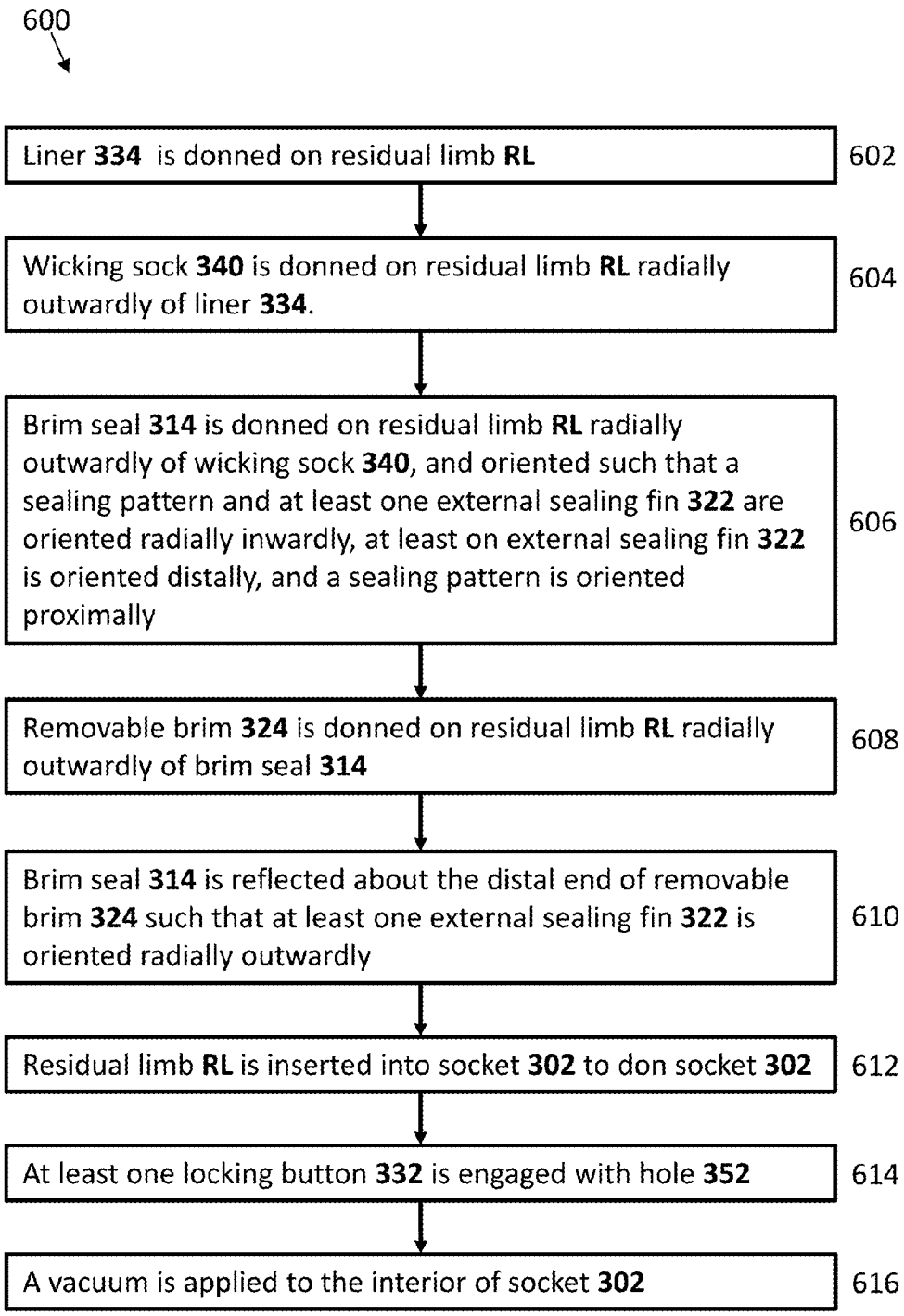
FIG. 6 is an example method for donning the socket sealing system 300.

FIG. 6 is an example method 600 for donning the socket sealing system 300. Liner 334 may be donned on residual limb RL. (Step 602). Wicking sock 340 may be donned on residual limb RL radially outwardly of liner 334. (Step 604). Brim seal 314 may be donned on residual limb RL radially outwardly of wicking sock 340, and oriented such that a sealing pattern (not shown) and at least one external sealing fin 322 are oriented radially inwardly, at least one external sealing fin 322 is oriented distally, and a sealing pattern (not shown) is oriented proximally. (Step 606). Removable brim 324 may be donned on residual limb RL radially outwardly of brim seal 314. (Step 608). Brim seal 314 may be reflected about the distal end of removable brim 324 such that at least one external sealing fin 322 is oriented radially outwardly. (Step 610). Residual limb RL may be inserted into socket 302 to don socket 302. (Step 612). At least one locking button 332 may be engaged with hole 352. (Step 614). A vacuum may be applied to the interior of socket 302. (Step 616).

Socket sealing system 300 may be doffed generally by following the steps of method 600 in reverse order.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available or prudent in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The invention claimed is:

1. A socket sealing system, comprising:
a prosthetic socket having a proximal end, an expanded section, and an internal peripheral shoulder;
a brim seal having an inner proximal end, an outer proximal end, and a distal end;
a removable brim having a distal end;
a liner; and
a wicking sock;
wherein prosthetic socket is oriented radially outwardly of the outer proximal end of the brim seal, the outer proximal end of the brim seal is oriented radially outwardly of the removable brim, the removable brim is oriented radially outwardly of the inner proximal end of the brim seal, the inner proximal end of the brim seal and the wicking sock are oriented radially outwardly of the liner; and
wherein the brim seal is reflected about the distal end of the removable brim.

2. The socket sealing system of claim 1, wherein the inner proximal end of the brim seal is oriented proximally.

3. The socket sealing system of claim 1, wherein the outer proximal end of the brim seal is oriented proximally.

4. The socket sealing system of claim 1, wherein the brim seal includes a sealing pattern extending radially inwardly, and wherein the sealing pattern engages the liner.

5. The socket sealing system of claim 1, wherein the brim seal includes at least one external sealing fin extending radially outwardly, and wherein the at least one external sealing fin engages the socket.

6. The socket sealing system of claim 1, wherein the distal end of the brim seal engages the internal peripheral shoulder of the socket.

7. The socket sealing system of claim 1, wherein the removable brim includes at least one locking button, wherein the socket includes at least one slot, and wherein the at least one locking button engages the at least one slot.

8. The socket sealing system of claim 1, wherein the socket includes at least one distal bypass valve.

\* \* \* \* \*